(12) United States Patent
Kinnan et al.

(10) Patent No.: US 8,709,487 B1
(45) Date of Patent: Apr. 29, 2014

(54) NANOPARTICLE ENTRAPMENT OF MATERIALS

(75) Inventors: Mark K. Kinnan, Albuquerque, NM (US); Heidi L. Schreuder-Gibson, Holliston, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 3 days.

(21) Appl. No.: 13/342,274

(22) Filed: Jan. 3, 2012

Related U.S. Application Data

(60) Provisional application No. 61/478,721, filed on Apr. 25, 2011.

(51) Int. Cl.
*A61K 9/51* (2006.01)

(52) U.S. Cl.
USPC .............................. 424/489; 977/773; 977/915

(58) Field of Classification Search
USPC ................................... 424/489; 977/773, 916
See application file for complete search history.

(56) References Cited

U.S. PATENT DOCUMENTS

| | | | |
|---|---|---|---|
| 6,632,671 | B2 | 10/2003 | Unger |
| 7,879,819 | B1 | 2/2011 | Sung et al. |
| 7,901,711 | B1 | 3/2011 | Sung et al. |
| 2008/0009558 | A1 | 1/2008 | Hawker et al. |
| 2011/0117623 | A1* | 5/2011 | Walker et al. .................. 435/182 |

* cited by examiner

*Primary Examiner* — Gina C Justice
(74) *Attorney, Agent, or Firm* — Roger C. Phillips, Esq.

(57) ABSTRACT

A water-based and surfactant-free microwave synthesis of polymer nanoparticles includes the entrapment of diisopropyl fluorophosphatase (DFPase) within poly(4-vinylpyridine) (PVP) nanoparticles. The resulting nanoparticles are approximately 80-100 nm in diameter and reactive activity of DFPase is maintained after encapsulation.

15 Claims, 5 Drawing Sheets

A solution containing: Solvent, Monomer, Crosslinker, Initiator, and Material (⊖) Target (e.g. Enzyme)

Nanoparticles with entrapped material

NANOPARTICLE ENTRAPMENT OF MATERIALS

CROSS-REFERENCE TO RELATED APPLICATIONS

This application claims priority to and the benefit from U.S. provisional application Ser. No. 61/478,721, filed on Apr. 25, 2011, the disclosure of which is incorporated herein by reference in its entirety.

BACKGROUND

1. Field

The aspects of the disclosed embodiments relate to a polymer based nanoparticle entrapment and, more particularly, to a method of synthesis of polymer based nanoparticles with entrapped materials that preserves the activity of the entrapped material.

2. Brief Description of Related Developments

Emulsion polymerization is an industry standard in the synthesis of colloidal polymers. Polymeric nanoparticles are used in a wide array of applications such as drug delivery systems, coatings, and cosmetics. Poly(4-vinylpyridine) (PVP) is a functional basic and nucleophilic polymer desirable for use as a nanoparticle because of the affinity of the pyridyl group to metals, its strong hydrogen-bonding with polar species, and its strong electrostatic interaction with charged surfaces, which allow them to be readily attached to surfaces of interest. Nanoparticles, including PVP, may be used to encapsulate chemical or biological materials such as, for example, bioactive agents, pharmaceutical agents, or enzymes, in order to protect the entrapped materials or prevent them from reacting with their environment. When encapsulating these materials, care must be taken to prevent degradation of the materials in order to preserve its efficacy or functional activity.

Generally, the synthesis of nanoparticles and nanocapsules requires the use of surfactants, organic solvents, heat, high pressure homogenization, or high intensity ultrasound sonication. However, these approaches can be problematic and can denature (if a biological material) or reduce efficacy of the active material to be encapsulated. Use of surfactants can change properties of the polymers, and removal of the surfactants is costly and time-consuming. Surfactant-free emulsion polymerization has emerged as a cleaner, simpler process of nanoparticle synthesis, as the nanoparticle surfaces are able to readily interact with the environment without the additional washing steps required to remove surfactants. Microwave heating has also been used in nanosphere polymerization reactions, for example in the synthesis of polystyrene, poly(methyl methacrylate), and other copolymer nanospheres. Microwave heating has also been shown to decrease reaction times and provide more uniformed heating yielding monodisperse nanospheres, when compared to conventional heating methods.

A process is therefore desirable which creates polymeric nanoparticles while preserving the activity of the entrapped materials. Specifically, it would be advantageous to have a rapid, surfactant-free, microwave synthesis of a nanoparticle entrapping an active material.

SUMMARY

One aspect of the disclosed embodiments relates to a method of synthesis. In one embodiment, the method includes preparing a reagent mixture in a reaction vessel, where the reagent mixture includes a monomer mixture, an aqueous initiator solution, and a material to be entrapped. The reagent mixture is irradiated with microwave radiation to obtain nanoparticles with entrapped materials.

In another aspect, the disclosed embodiments relate to a method of synthesis. In one embodiment, the method includes preparing a reagent mixture in a reaction vessel, the reagent mixture including a monomer to be polymerized, a crosslinker, an aqueous initiator solution, and an enzyme. The reagent mixture is irradiated with microwave radiation to obtain nanoparticles with encapsulated enzyme.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and unless otherwise indicated, they are merely intended to conceptually illustrate the structures and procedures described herein. In addition, any suitable size, shape or type of elements or materials could be used.

DETAILED DESCRIPTION OF THE DISCLOSED EMBODIMENTS

The aspects of the disclosed embodiments relate particularly to a rapid, surfactant-free microwave synthesis method of monodisperse poly(4-vinylpyridine) (PVP) nanospheres, and similar method of synthesizing nanospheres or nanocapsules with entrapped active materials. While the description sets forth the various embodiments with specific experimental details, it will be appreciated that the description is illustrative only and should not be construed in any way as limiting the invention. Unless otherwise noted, all stated ranges are inclusive of endpoints. It is understood that all ranges are approximations and can vary depending on the materials used for the reaction.

The method according to the disclosed embodiments is water-based, thus avoiding the use of harmful solvents or surfactants that must be washed and removed. Additionally, the method is carried out at relatively low temperatures through microwave radiation. The mild nature of this process makes it ideal for use with sensitive active compounds, such as enzymes, therefore making it suitable for forming nanoparticles that entrap or encapsulate certain sensitive materials.

The entrapment or encapsulation of sensitive materials, such as enzymes and pharmaceutical actives or other bioactive agents, in polymer nanoparticles allows for protection of the active material against degradation due to contact with the environment. When used with pharmaceutical compounds, the encapsulation can allow for a slow release of the drug entrapped in the nanoparticle. In the case of enzymes, the encapsulation reduces diminishment of the enzyme properties when exposed to organic solvents or extreme temperatures. One particular application for encapsulated enzymes is in the transformation of harmful chemicals into harmless products, such as the break-down of chemical warfare agents. For example, DFPase encapsulated in a PVP nanoparticle could be used to decontaminate diisopropyl fluorophosphate (DFP), which is a potent neurotoxin and chemical warfare agent simulant.

Figure 1:
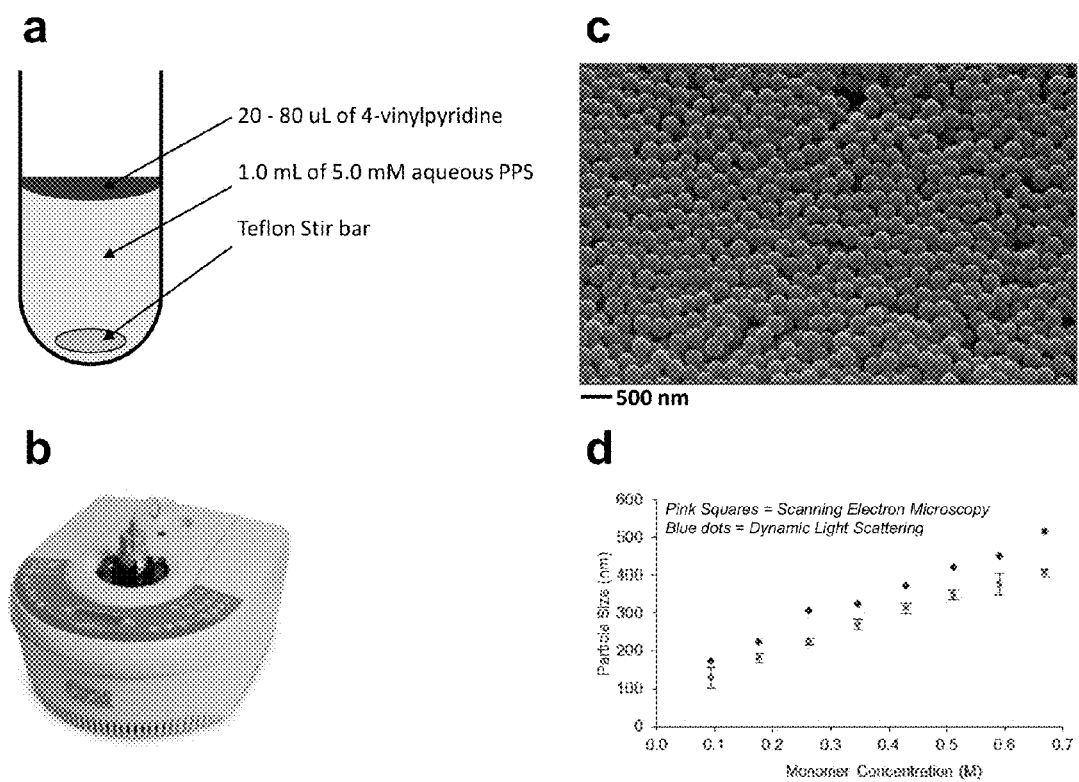
FIG. 1a is an illustration of a reaction mixture for polymerization of PVP in accordance with an embodiment of the disclosure.
FIG. 1b is an illustration of an exemplary microwave unit for use in the method according to an embodiment of the disclosure.
FIG. 1c is a scanning electron microscopy (SEM) image of PVP nanoparticles formed by the method according to an embodiment of the disclosure.
FIG. 1d is a graph illustrating the effect of monomer concentration on particle size.
Figure 2:
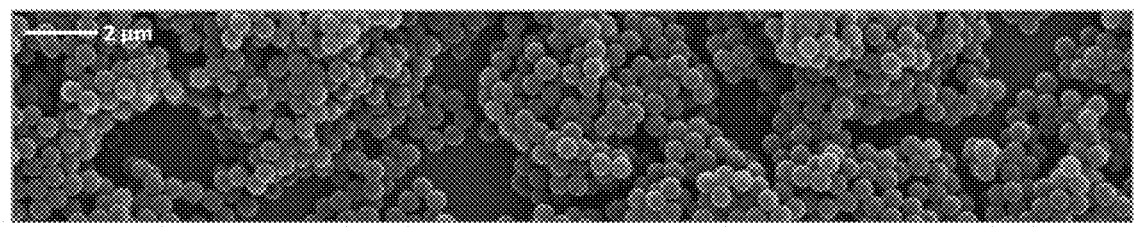
FIG. 2 is a SEM image of PVP nanoparticles without encapsulated enzyme
Figure 3:
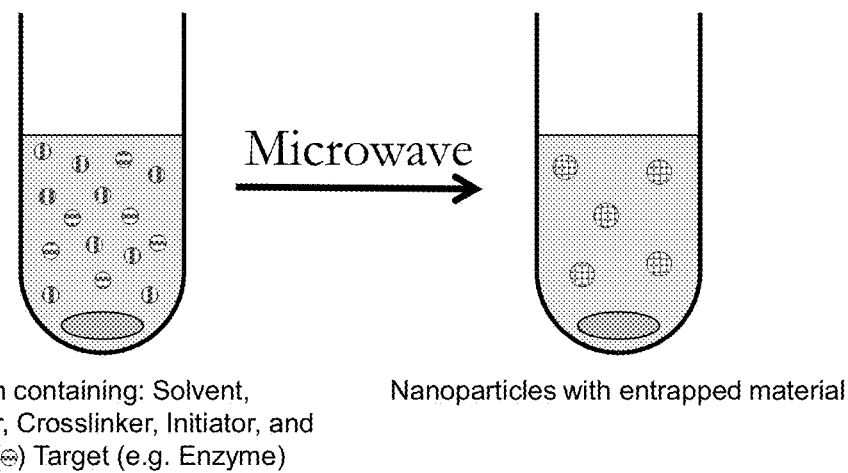
FIG. 3 is an illustration of a method of microwaving reaction ingredients to synthesize nanoparticles with entrapped materials in accordance with an embodiment of the disclosure.
Figure 4:
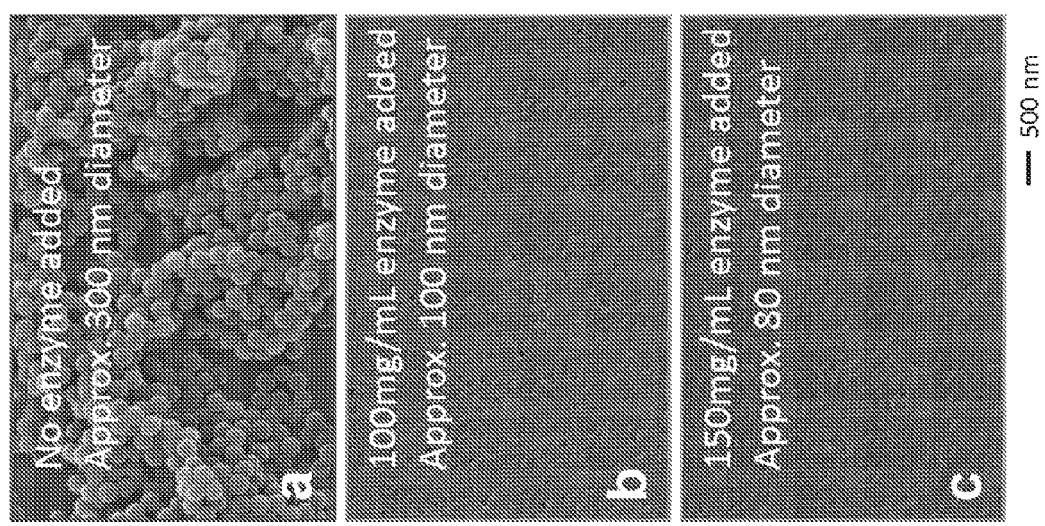
FIG. 4 shows SEM images of PVP nanoparticles without and with encapsulated enzyme.
Figure 5:
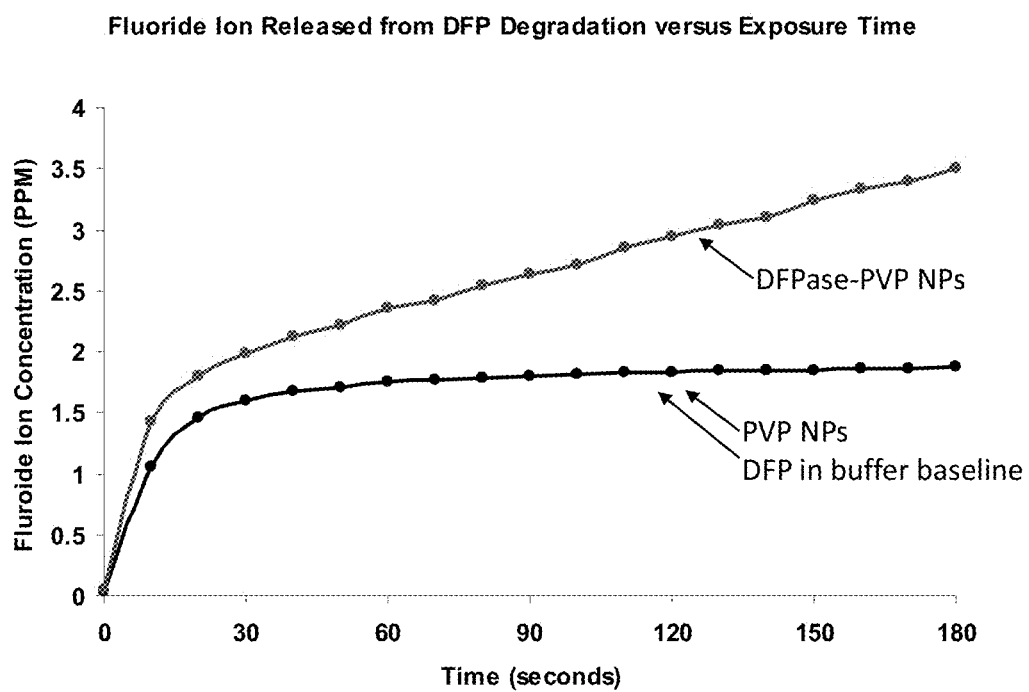
FIG. 5 is a chart illustrating the breakdown of DFP by PVP nanoparticles and PVP/DFPase nanocapsules.

Referring to FIG. 1*a*, a synthesis method for producing PVP nanoparticles or nanospheres without encapsulated active is presented. In the embodiment of FIG. 1, a monomer mixture, including a monomer (4-vinylpyridine) and a crosslinker, is combined with an aqueous solution containing a polymerization initiator, in a vessel. After microwave treatment of the vessel, including the entire reaction mixture, monodisperse PVP nanoparticles are formed, as are shown in the SEM image of FIG. 1*b*.

Referring to FIG. 3, a method of forming nanoparticles with entrapped materials is illustrated. Reagents include a material to entrap, a monomer to be polymerized, a polymerization initiator, and a crosslinker. First, these reaction ingredients are combined in a reaction vessel in no particular order. Next, the vessel, and the entire reaction mixture, is microwave treated in order to produce the nanocapsules containing the active material. In one embodiment, the reaction forms PVP nanoparticles. In alternate embodiments, the nanoparticles may be any polymer suitable for entrapping biological or chemical materials.

In the example of FIG. 3, the reagent mixture includes a monomer and a crosslinker, however, in alternate embodiments, the reaction may be successful if the crosslinker is omitted from the reagent mixture. Similarly, the reagent mixture may contain one chemical that acts as both monomer and crosslinker. In a further embodiment, the reagent mixture that acts as monomer, crosslinker and material to entrap, if the chemical has all the necessary chemical functional groups for making/crosslinking into nanoparticles while still maintaining its reactive function. Any suitable combinations of at least one monomer, or at least one monomer plus crosslinker may be used.

In the embodiment of FIG. 3, PVP nanoparticles are synthesized in the presence of secondary compounds that serve as templates, or cores, for the polymer shell, thus encapsulating or entrapping the secondary material within the nanoparticle. The water-based and low-temperature nature of the method makes it suitable for the encapsulation of sensitive compounds, such as enzymes, as the activity and chemical nature of the compounds are preserved during the encapsulation.

In one embodiment, the secondary material or active agent encapsulated is DFPase. In alternate embodiments, the secondary material can be any chemical or biological material, such as an enzyme, bioactive agent, or pharmaceutical agent exhibiting active properties that would benefit from encapsulation.

FIG. 4 shows SEM images of PVP nanoparticles with and without encapsulated DFPase enzyme that were formed according to the method of the disclosed embodiments. In FIG. 4*a*, nanoparticles formed without the addition of enzyme are approximately 300 nm in diameter. Adding 100 mg/mL of enzyme reduces nanoparticle diameter to approximately 100 nm (FIG. 4*b*), while addition of 150 mg/mL enzyme reduces nanoparticle diameter to 80 nm. The presence of the enzyme therefore is proven to reduce the diameter of nanoparticles formed using the water-based microwave polymerization.

FIG. 5 illustrates an experiment showing the breakdown of DFP by the PVP/DFPase nanocapsules. Breakdown of DFP is measured by the presence of fluoride ion. More fluoride ions produced indicates more reaction has occurred. Results of the experiment show that the encapsulated DFPase enzyme is a more effective decontaminant of DFP than the polymer nanoparticles without encapsulant. While encapsulating the DFPase in the nanoparticles does reduce the activity of the DFPase compared to unencapsulated DFPase, the encapsulation makes the enzyme more stable for long periods of time. The reduced denaturation of the encapsulated enzyme makes it a more effective decontaminant of DFP.

Specific laboratory examples are provided below. It is understood that these specific examples and the material concentrations, times, and other experimental parameters and reaction conditions are not meant to limit the scope of the invention and allow for variations depending on the types of materials employed. Materials for use may include the following listing of suitable chemicals and conditions for practicing the method according to the disclosed embodiments:

Monomers are selected from chemical molecules that polymerize via traditional addition polymerization mechanisms and can include, for example, alkenes, vinyl group-containing molecules and derivatives and similar compounds, and equivalent alkene containing structures having one or more double bonds that are polymerizable via addition polymerization, such as acrylonitrile, and are not limited to the 4-vinylpyridine mentioned in the examples below.

In addition to the potassium persulfate (KSP) mentioned in the examples below, other exemplary initiators can include 4,4' Azobis(4-cyanovaleric acid), peroxydisulfates, azo compounds, peroxides, and equivalents that are capable of activation (generation of one or more free radical) by microwave radiation. Any suitable initiator can be used.

Exemplary crosslinkers include, but are not limited to, ethylene glycol dimethacrylate (EGDMA), ethylene glycol diacrylate, N,N'-methylenebisacrylamide, and other equivalent substances.

Solvents are hydrophilic and water-based and may be 100% water, or a mixture of water and other hydrophilic solvents including, for example, aldehydes/ketones, alcohols and other equivalents.

Example No. 1

Surfactant-Free Microwave Synthesis of PVP Nanospheres

A monomer mixture of 4-vinylpyridine (monomer) and ethylene glycol dimethacrylate (EGDMA, crosslinker) were combined to create a 54:1 monomer:crosslinker mole ratio solution. The reaction mixture was created by adding 20-60 μL (0.18-0.59 M) of monomer mixture to 1.0 mL of an aqueous 5.0 mM potassium persulfate (KPS) solution in a 10-mL glass microwave reaction vessel containing a small Teflon-coated, magnetic stirring bar, as illustrated in FIG. 1a. Upon addition of the monomer mixture to the aqueous solution, the mixture phase-separated into water (clear) and monomer (brown) phases. The solution was not emulsified. Slow mixing of the reagents was performed for 5 minutes. Upon microwave heating (FIG. 1b), the solution temperature rapidly increased to 90° C. during the first 60 s of heating and only increased a few additional degrees throughout the remainder of the heating sequence. At the end of the microwave heating, the reaction was rapidly air-cooled to 30° C. using the air-cooling feature of the microwave. The contents of the reaction vessel contained a white, opaque suspension of nanospheres in the aqueous phase.

It was observed that monomer mixture concentration (monomer plus crosslinker) had the greatest impact on the size of the nanospheres. As illustrated in the graph of FIG. 1d, using the conditions 5.0 mM KPS, 70 W microwave power, and 3 min microwave time it was found that the size of the nanospheres increased linearly with monomer mixture concentration over the range 0.094 M to 0.67 M.

In a preferred embodiment, to obtain the highest yield of nanospheres (77.9±2.1%) regardless of particle size, the preferred parameters are 70 W of power, 2 minutes of microwave time, and a monomer mixture concentration of 0.43 M. However, in another embodiment, crosslinked PVP nanospheres are successfully synthesized using 30 to 110 W of microwave power, 1 to 5 minutes of microwave treatment, and 0.26 to 0.75 M of monomer mixture concentration. The above mentioned parameters and ranges are inclusive of all endpoints and are not meant to be limiting in scope. In alternate embodiments, parameters outside of the stated ranges may successfully produce PVP nanospheres and are considered within the scope of the invention.

Example 2

Surfactant-Free Microwave Synthesis of PVP Nanoparticles with Entrapped Material 20-80 µL of monomer mixture (a 1:20 ratio of 4-vinylpyridine (monomer) to pentaerythritol tetraacrylate (crosslinker)) and 5-150 mg of DFPase were added to 1.0 mL of an aqueous 5.0 mM potassium persulfate (KPS) solution in a 10-mL glass microwave reaction vessel containing a small Teflon-coated, magnetic stirring bar. The reaction was carried out in a closed vessel. Upon addition of the monomer mixture to the aqueous solution, the mixture phase-separated into water (clear) and monomer (brown) phases. The mixture was then microwave irradiated at 40-70 W. Upon microwave heating, the solution temperature rapidly increased to 90° C. during the first 60 seconds of heating and only increased a few additional degrees throughout the remainder of the 1-6 minute heating sequence (preferably 3-5 minutes). At the end of the microwave heating, the reaction was rapidly air-cooled to 30° C. using the air-cooling feature of the microwave. The contents of the reaction vessel contained a white, opaque suspension of nanospheres in the aqueous phase. Successful encapsulation of DFPase in the nanoparticles was achieved. Enzyme activity was tested and the enzyme was found to retain the original reactive activity levels.

In one embodiment, in the reaction of Example 2, the monomer mixture concentration of the reagent mixture is approximately 0.18-0.59 M. In alternate embodiments, the monomer mixture concentration can be as little or as much as desired, for example, 0.01-0.1M.

The aspects of the disclosed embodiments provide a method of water-based, surfactant-free, microwave synthesis of nanoparticles, and in particular, synthesis of PVP nanoparticle-encapsulated DFPase.

Thus, while there have been shown, described and pointed out, fundamental novel features of the invention as applied to the exemplary embodiments thereof, it will be understood that various omissions and substitutions and changes in the form and details of devices illustrated, and in their operation, may be made by those skilled in the art without departing from the spirit of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of synthesis comprising:
    preparing a reagent mixture in a reaction vessel, the reagent mixture maintaining at least two separated phases and comprising:
        a monomer mixture comprising at least one monomer to be polymerized,
        an aqueous initiator solution, and
        a material to be entrapped, and
    irradiating the reagent mixture with microwave radiation to obtain nanoparticles with entrapped materials;
    wherein the nanoparticles with entrapped materials are synthesized using 30 to 110 W of microwave power, 1 to 6 minutes of microwave radiation, and 0.01 to 0.75 M concentration of the monomer mixture.

2. The method according to claim 1 wherein the monomer mixture further comprises a crosslinker.

3. The method according to claim 2 wherein the monomer is 4-vinylpyridine.

4. The method according to claim 1 wherein the concentration of the monomer mixture is 0.01-0.1M.

5. The method according to claim 1 wherein the concentration of the monomer mixture is approximately 0.18-0.59 M.

6. The method according to claim 1 wherein the aqueous initiator solution comprises about 5.0 mM potassium persulfate solution.

7. The method according to claim 1 wherein the reagent mixture is irradiated for a period of time from 3 to 5 minutes.

8. The method according to claim 1 wherein the material to be entrapped is a biological material.

9. The method according to claim 8 wherein the material to be entrapped is an enzyme, a bioactive agent, or a pharmaceutical agent.

10. A method of synthesis comprising:
    preparing a reagent mixture in a reaction vessel, the reagent mixture maintaining at least two separated phases and comprising:
        a monomer to be polymerized,
        an aqueous initiator solution, and
        an enzyme;
    irradiating the reagent mixture with microwave radiation to obtain nanoparticles with encapsulated enzyme;
    wherein the nanoparticles with encapsulated enzyme are synthesized using 30 to 110 W of microwave power, 1 to 6 minutes of microwave radiation, and a 0.01 to 0.75 M monomer concentration of the reagent mixture.

11. The method according to claim 10 wherein the resulting nanoparticles have a diameter ranging from 80-100 nm.

12. The method according to claim 10 wherein the monomer to be polymerized is 4-vinylpyridine.

13. The method according to claim 10 wherein the enzyme is diisopropyl fluorophosphatase.

14. The method according to claim 10 wherein an original reactivity of the enzyme is maintained within the resulting nanoparticle.

15. The method according to claim 10 wherein the reagent mixture further comprises a crosslinker.

* * * * *